United States Patent [19]

Leonard

[11] Patent Number: 5,539,000
[45] Date of Patent: Jul. 23, 1996

[54] SPRAY-CHILLED NABUMETONE

[75] Inventor: Graham S. Leonard, Welwyn Garden City, England

[73] Assignee: SmithKline Beecham p.l.c., Brentford, England

[21] Appl. No.: 30,331

[22] PCT Filed: Jan. 22, 1993

[86] PCT No.: PCT/GB93/00145

§ 371 Date: Feb. 22, 1993

§ 102(e) Date: Feb. 22, 1993

[87] PCT Pub. No.: WO93/14747

PCT Pub. Date: Aug. 5, 1993

[30] Foreign Application Priority Data

Jan. 29, 1992 [GB] United Kingdom ............. 9201857

[51] Int. Cl.[6] .................................................. A61K 31/12
[52] U.S. Cl. .................................................. 514/682
[58] Field of Search .................................................. 514/682

[56] References Cited

U.S. PATENT DOCUMENTS

| 4,086,346 | 4/1978 | Bocker et al. | 424/253 |
| 4,420,639 | 12/1983 | Lake et al. | 568/328 |

FOREIGN PATENT DOCUMENTS 0362731  4/1990  European Pat. Off. .

OTHER PUBLICATIONS

Chemical Abstracts, vol. 108, No. 12, 21 Mar. 1988, Columbus, Ohio, US; abstract No. 101197y, E. A. Daigneault et al. 'bioeqiuvalence study of nabumetone: tablet versus suspension' p. 436; column 2; see abstract & Am. J. Med. 1987, 83(4B).

*Primary Examiner*—Marianne M. Cintins
*Assistant Examiner*—Keith MacMillan
*Attorney, Agent, or Firm*—Stephen Venetianer; Edward T. Lentz

[57] ABSTRACT

Nabumetone which is spray-chilled and formulated into unit dose forms which have a smaller volume than was previously possible.

8 Claims, No Drawings

SPRAY-CHILLED NABUMETONE

This application is a 371 of PCT/GB93/00145 filed Jan. 22, 1993.

BACKGROUND OF THE INVENTION

The present invention relates to spray-chilled nabumetone and a process for its manufacture.

GB 1,474,377 describes a non-steroidal anti-inflammatory drug 4-(6-methoxy- 2-naphthyl)-butan-2-one which is Commonly known as nabumetone. This patent also describes a process for the manufacture of nabumetone.

Nabumetone is most commonly prescribed as 500 mg or 1000 mg swallow tablets. The resulting tablets containing nabumetone and conventional excipients are fairly large in size and can be a problem to swallow for some patients.

Conventionally isolated and milled nabumetone has a poured density range of 0.35 to 0.39 $gcm^{-3}$ and a tapped density range of 0.44 to 0.48 $gcm^{-3}$ and when mixed with conventional excipients produces a tablet volume of 0.485 $cm^3$ for a 500 mg nabumetone tablet and a volume of 0.970 $cm^3$ for a 1000 mg nabumetone tablet.

Conventionally isolated and milled nabumetone is formulated into conventional swallow tablets by admixing with conventional fillers, surfactants and disintegrants. It has been found that the maximum amount of drug that can be mixed with excipients, especially fillers, is 82%. Increasing the percentage of drug further (i.e. reducing the percentage of excipients, especially fillers) causes the tablet to be prone to breaking up on manufacture, storage and transportation, which is obviously a disadvantage.

Spray-chilling is a technique that has been in existence for approximately 30 years, and has been applied to the production of food-stuffs such as coffee as well as pharmaceuticals.

Spray-chilling is usually chosen because it is a process which produces uniform product qualifies such as particle size, moisture content and bulk density.

In pharmaceutical production, spray-chilling is used because it can provide products which have improved flow characteristics.

SUMMARY OF THE INVENTION

It has now been found that spray chilled nabumetone has excellent formulation properties, is cheaper to produce and can be surprisingly formulated into viable tablets using fewer excipients than were previously needed. Furthermore, spray-chilled nabumetone has the unexpected advantage of being more dense than conventionally isolated and milled nabumetone and can therefore be formulated into smaller tablets which are easier to swallow.

DESCRIPTION OF THE PREFERRED EMBODIMENTS

Accordingly, the present invention provides spray-chilled nabumetone.

The present invention further provides spray-chilled nabumetone having a poured density range of 0.40 to 0.65 $gcm^{-3}$.

In particular, the poured density range of spray-chilled nabumetone is suitably between 0.45 and 0.60 $gcm^{-3}$ or more preferably 0.5 to 0.55 $gcm^{-3}$ Most preferably the poured density of spray-chilled nabumetone is about 0.5 $gcm^{-3}$.

The present invention also provides spray-chilled nabumetone having a tapped density range of 0.50 to 0.65 $gcm^{-3}$.

In particular, the tapped density range of spray-chilled nabumetone is suitably between 0.54 to 0.62 $gcm^{-3}$ or more preferably between 0.58 to 0.62 $gcm^{-3}$. Most preferably the tapped density of spray-chilled nabumetone is about 0.60 $gcm^{-3}$.

The present invention also provides a pharmaceutical composition containing spray-chilled nabumetone admixed with a pharmaceutically acceptable carrier.

It should be appreciated that the term excipient hereinafter used means a pharmaceutically acceptable carrier.

Another aspect of the present invention provides spray-chilled nabumetone in unit dose form. Suitable unit dose forms include tablets, sachets, suspensions and suppositories containing nabumetone, which are formed using conventional techniques known in the art of formulation science.

The invention yet further provides a swallow tablet containing 500 mg of spray-chilled nabumetone admixed with conventional excipients which tablet has a volume of 0.429 $cm^3$. Thus, the present invention provides swallow tablets containing 500 mg of spray-chilled nabumetone having a volume of less than 0.480 $cm^3$, preferably less than 0.450 $cm^3$ and most preferred less than 0.430 $cm^3$.

The invention also provides a swallow tablet containing 1000 mg of spray-chilled nabumetone admixed with conventional excipients which tablet has a volume of 0.858 $cm^3$. Thus, the present invention provides swallow tablets containing 1000 mg of spray-chilled nabumetone having a volume of less than 0.960 $cm^3$, preferably less than 0.930 $cm^3$, and most preferably less than 0.860 $cm^3$.

The present invention also provides a unit dose formulation of spray-chilled nabumetone prepared using no or substantially no conventional filling agents as excipients.

It should be appreciated that filling agents are those conventionally recognised in the art of formulation science such as micro-crystalline cellulose, hydroxy propylmethylcellulose, lactose and starch.

The present invention also provides conventional swallow tablets in which the percentage (w/w) of spray-chilled nabumetone to excipient is in excess of 82%, suitably it is in excess of 85%, even more suitably it is in excess of 88% and preferably it is in excess of 90%.

Another aspect of the present invention provides a process for preparing spray-chilled nabumetone which comprises melting solid nabumetone, spraying it into a chiller-chamber of a spray-chiller and collecting the resulting product.

Nabumetone is preferably melted by heating it to 20° C. above its melting point (80°).

The melted nabumetone is suitably fed into the chiller-chamber at 16–17 kg/hr.

The chiller-chamber is suitably cooled to 1°–4° C.

The nabumetone is suitably fed into the chiller-chamber via a 2 fluid nozzle, is atomised using hot compressed air and the resulting product is suitably collected in a cyclone.

The spray-chiller used above is suitably a conventional commercially available spray-chiller.

The nabumetone for use in spray-chilling is suitably prepared according to the procedures outlined in EP-A-0 003074 (Beecham Group plc) or EP-A-0 288144 (Beecham Group plc), although it should be appreciated that nabumetone prepared by any suitable means may be used for spray-chilling.

Nabumetone is previously described as being useful for treating inflammation, especially that resulting from rheumatoid or oesteoarthritis, sprain, strains, cancer pain, fever, oesteoporosis and myofacial pain syndrom. The present invention therefore provides a method of treatment of inflammation, sprains, strains, cancer pain, fever, oesteoporosis and myofacial pain syndrome which comprises administering an effective amount of spray-chilled nabumetone to a sufferer in need thereof.

The present invention also provides the use of spray-chilled nabumetone in the manufacture of a medicament for treating inflammation, sprains, strains, cancer pain, fever, oesteoporosis and myofacial pain syndrome.

The present invention further provides a pharmaceutical composition for use in the treatment of inflammation, sprains, strains, cancer pain, fever, oesteoporisis and myofacial pain syndrome which comprises spray-chilled nabumetone admixed with pharmaceutically acceptable carriers.

The following examples describe the preparation of spray-chilled nabumetone and the formation of swallow tablets containing 500 mg and 1000 mg of nabumetone respectively.

EXAMPLE 1

PREPARATION OF SPRAY-CHILLED NABUMETONE

Nabumetone prepared by the process described in EP-A-0 003 074 was melted (80° C.) and held at about 100° C. The melt was then fed into the chiller chamber of a conventional spray-chiller using a peristaltic pump at a feed rate of 16–17 kg/hr via a 2 fluid (air atomising) nozzle where it is atomized using hot compressed air at 80 psi (S.I. units required).

The sprayed nabumetone was then cooled as it was sprayed into the chiller-chamber, which was maintained at 1°–4° C., and the crystallised product was collected in a cyclone.

The spray chiller used above is commercially available from Drytech Ltd, 46 Morley Road, Tonbridge, Kent, UK.

EXAMPLE 2

(500 mg spray-chilled nabumetone swallow tablet)
The following were mixed in a conventional manner and compressed to form a swallow tablet.

| | |
|---|---|
| 500 mg | Spray Chilled Nabumetone |
| 25 mg | *Explotab |
| 2 mg | Sodium lauryl sulphate |
| 527 mg | |

EXAMPLE 3

(1000 mg spray-chilled nabumetone swallow tablet)
The following were mixed in a conventional manner and compressed to form a swallow tablet.

| | |
|---|---|
| 1000 mg | Spray Chilled Nabumetone |
| 50 mg | *Explotab |
| 4 mg | Sodium lauryl sulphate |
| 1027 mg | |

*Trademark for sodium starch glycollate.

I claim:
1. Spray-chilled nabumetone in unit dosage form which has no or substantially no filling agents as excipients.
2. Spray-chilled nabumetone having a poured density range of 0.40 to 0.65 gcm$^{-3}$ which has no or substantially no filling agents as excipients.
3. Spray-chilled nabumetone having a tapped density range of 0.50 to 0.65 gcm$^{-3}$ which has no or substantially no filling agents as excipients.
4. A pharmaceutical composition containing spray-chilled nabumetone according to claim 1 admixed with a pharmaceutically acceptable carrier.
5. A unit dose form according to claim 1 which is a swallow tablet containing 500 mg of spray-chilled nabumetone admixed with conventional excipients which tablet has a volme of less than 0.480 cm$^3$.
6. A unit dose form according to claim 1 which is a swallow tablet containing 1000 mg of spray-chilled nabumetone admixed with excipients which tablet has a volume of less than 0.960 cm$^3$.
7. A swallow tablet according to claim 5 in which the percentage (w/w) of spray-chilled nabumetone to excipient is in excess of 82%.
8. A swallow tablet according to claim 7 in which the percentage of spray-chilled nabumetone to excipient is in excess of 90%.

* * * * *